United States Patent [19]

Shamos et al.

[11] 3,997,838
[45] Dec. 14, 1976

[54] APPARATUS AND METHOD FOR MEASUREMENT OF TOTAL VOLUME OF PARTICLES IN A LIQUID SAMPLE

[75] Inventors: Morris H. Shamos, Bronx; Michael J. Brand, Somers; William J. Calogero, Hopewell Junction, all of N.Y.

[73] Assignee: Technicon Instruments Corporation, Tarrytown, N.Y.

[22] Filed: Apr. 14, 1975

[21] Appl. No.: 567,784

[52] U.S. Cl. .................. 324/71 R; 128/2.05 V; 128/2 G; 324/71 CP; 204/195 R
[51] Int. Cl.² ................. G01N 27/26; G01N 27/00
[58] Field of Search .......... 324/71 CP, 71 R, 29 R; 73/203, 194 E; 128/2 G, 2.05 V; 204/195 R

[56] References Cited

UNITED STATES PATENTS

| | | | |
|---|---|---|---|
| 3,549,994 | 12/1970 | Rothermel et al. | 324/71 |
| 3,566,950 | 1/1971 | Dahms | 204/1 |
| 3,654,113 | 4/1972 | Bochinski | 204/195 R |
| 3,746,506 | 10/1973 | Platt | 204/195 R |

OTHER PUBLICATIONS

"Computer Approach to Ion–Selective Electrode Potentiometry by Standard Addition Methods," Brand & Rechnitz Analytical Chemistry, vol. 42, No. 11, Sept. 1970, pp. 1172–1177.

Primary Examiner—Robert Segal
Assistant Examiner—Vincent J. Sunderdick
Attorney, Agent, or Firm—S. P. Tedesco; Stephen E. Rockwell

[57] ABSTRACT

Apparatus and method, utilizing an ion-selective electrode and a reference electrode, for determining the percentage volume of total particulates in a predetermined volume of a liquid medium or sample having an effective known concentration of a particular ion. The method includes introducing a predetermined volume of a diluent having a known concentration of that ion into the sample, and measuring with the electrodes the concentration of that ion in the diluted sample to indicate the percentage volume of total particulates in the sample. The apparatus and method for such determination are well suited for determining the percentage volume of total cells in a sample of whole blood.

19 Claims, 2 Drawing Figures

APPARATUS AND METHOD FOR MEASUREMENT OF TOTAL VOLUME OF PARTICLES IN A LIQUID SAMPLE

BACKGROUND OF THE INVENTION

1. Field of the Invention

This invention relates to the determination of the percentage volume of total particulates in a liquid sample utilizing an ion-selective electrode and a reference electrode.

2. Prior Art

The use of ion-selective electrodes for the measurement in whole blood or other liquid samples of the concentration of dissolved constituents such as sodium, potassium and calcium, for example, is well known. It is also known that such samples may be "spiked" with a diluent containing the same ion to which the electrode is selective in the aforementioned measuring process. This is commonly known as "standard addition analysis".

The determination of the percentage volume of total particulates in a liquid sample is useful for many purposes. For example, the percentage volume of red cells in blood, known as hematocrit, is an important clinical parameter for diagnostic use. The percentage volume of all cells in blood in most cases is essentially equivalent to hematocrit, and is also of interest though it includes the percentage volume of white cells. However, in cases of persons with relatively high white cell counts, e.g., persons having leukemia, the percentage volume of total cells and hematocrit are not essentially the same. This limitation is recognized and it is believed that it does not represent a serious problem as a white cell count determination of such blood may be made in a conventional manner.

Heretofore, hematocrit has been most commonly determined by centrifuging in a capillary tube a volume of whole blood to separate the blood into a cell portion, a heavier phase, and a serum or plasma portion, a lighter phase. This is followed by estimation, using a manual technique, of the total blood volume and the cell volume, or by automatic determination as in accordance with the teaching of Adler et al. U.S. Pat. No. 3,684,450. Colorimetric determination of hematocrit is described by E. Ponder: *Hemolysis and Related Phenomena*, pp 51-53, Grune and Straton, N.Y., 1948. Such colorimetric determination also requires, among other things, such as dye addition, centrifuging of a portion of the sample. Determination of the percentage volume of blood cells by conductimetric techniques is also known. Beaver U.S. Pat. No. 3,648,260 describes two such techniques, the preferred and most accurate one of which also requires centrifuging of a sample portion. The other technique described by the last-mentioned patent does not require centrifuging of the sample, but this technique requires an assumption of a mean value for the conductivity of plasma. The conductivity of plasma arises from the presence of ions produced by dissociation of salts, e.g., sodium and chloride ions. Variation in the conductance of plasma, as found in at least certain diseased states, introduces significant errors in such a cell volume determination. E. Ponder, Supra, also describes, among the general types of techniques discussed above, diffractometric and photographic determinations (pp 62-79) of hematocrit, which are both optical techniques not requiring centrifuging of a whole blood sample, utilizing a diffraction pattern and a photographic image, respectively, of a thin film of cells to estimate the mean cell diameter and volume. Both the diffractometric and photographic methods require a red cell count of the blood sample as by inspection of a thin film of blood under a microscope for example. Hematocrit is then calculated from the estimated values of mean red cell volume and red cell count. Yet another method of determining hematocrit involves passing the diluted blood sample through a small orifice and measuring the electrical resistance changes which occur across the orifice. The frequency and magnitude of such changes are related to the cell count and to the mean cell volume, respectively, from which parameters hematocrit is calculated.

The present invention seeks to overcome difficulties encountered with such prior techniques of determining the percentage volume of total cells in blood, in large part by avoidance of centrifuging or determining the red cell count of a sample of whole blood which is time consuming and requires relatively expensive apparatus.

SUMMARY OF THE INVENTION

One object of the invention is to provide an improved apparatus and method for determining the percentage volume of total particulates of many kinds in many different liquid media, which are well suited to determining the percentage volume of total cells in whole blood. The invention involves the use of an ion-selective electrode and a reference electrode for the measurement of the concentration of a particular ion which may occur naturally in a liquid medium at significant levels, e.g., sodium, potassium and chloride in human blood. If the liquid medium does not have a naturally occurring concentration of a particular ion at such levels, it is considered for purposes herein as being free of such ion but may be "spiked" with a significant concentration of that particular ion for such electrode measurement. The determination of percentage volume of particulates in a liquid sample is well suited in many instances to continuous-flow-type analysis and is fast and accurate. The method of such determination includes introducing a predetermined volume of a diluent having a known concentration of the particular ion into a known volume of the sample, and measuring with the ion-selective electrode and the reference electrode the concentration of the particular ion in the diluted sample to indicate the percentage volume of total particulates in the sample. The basis of the method is that the ion-selective electrode and the reference electrode measure the concentration of the particular ion in the liquid phase unaltered by the presence of the particulate phase. The total volume of the sample is the sum of the volume of the liquid phase and the volume of the particulate phase. Dilution of the total sample with the diluent effectively only dilutes the liquid phase of the sample. The known concentration of the particular ion in the diluent and in the sample before dilution, together with measurement of the particular ion concentration after dilution, provides the data required for determination of the volume of the sample liquid phase prior to dilution. Subtraction of the volume of the liquid phase from the known sample volume gives the volume of the particulate phase, which is expressed as a percentage volume of the total sample volume.

DETAILED DESCRIPTION OF THE PREFERRED EMBODIMENTS

Figure 1:
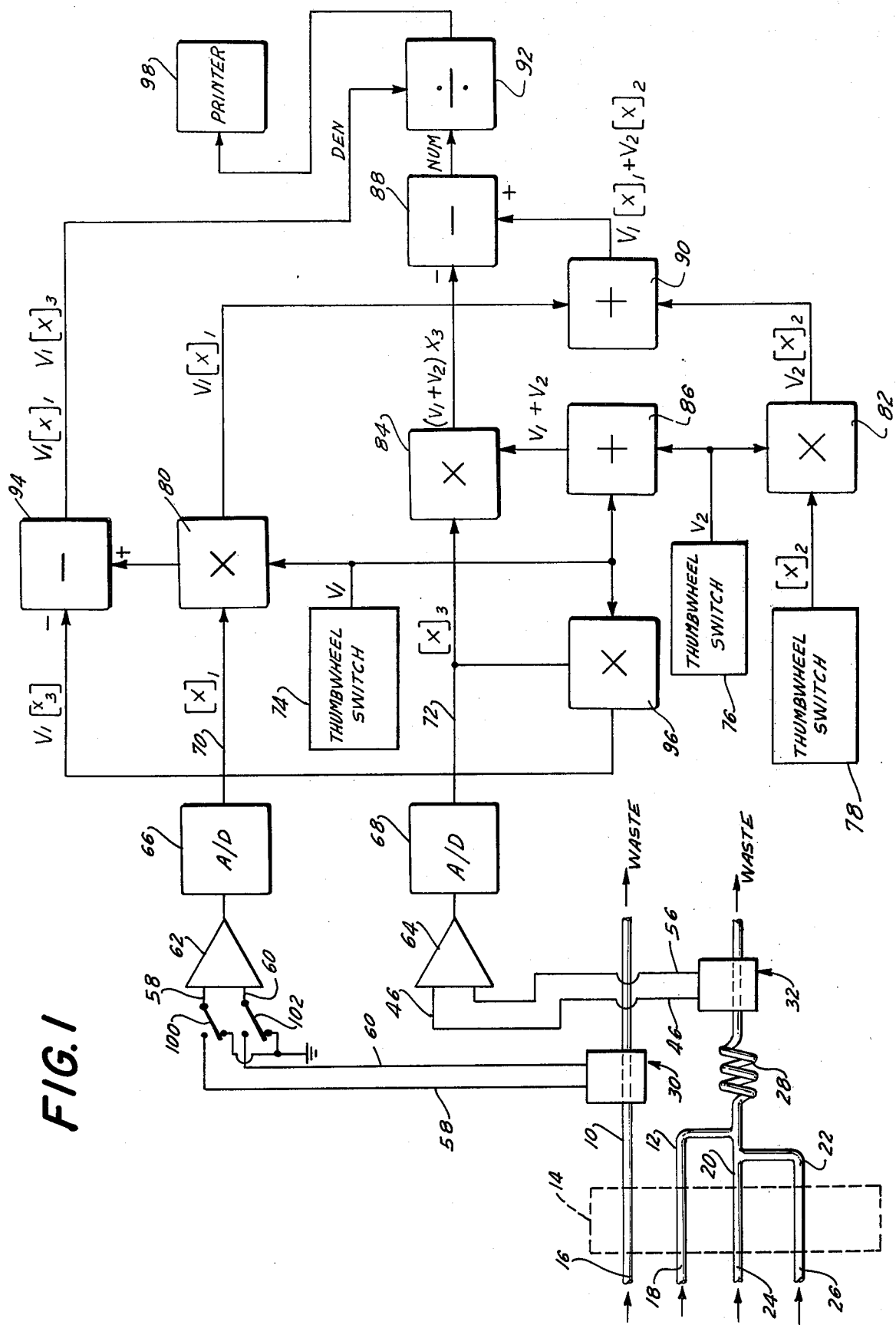
FIG. 1 is a schematic view illustrating apparatus embodying the invention.

As shown in FIG. 1, compressible pump tubes 10, 12 extend through a peristaltic pump 14 and have inlet ends 16 and 18, respectively, which may be concurrently supplied in a nonillustrated manner by a conventional sampler, similar to that described in de Jong U.S. Pat. No. 3,134,263, with aliquots of a same liquid sample which is one of a series of such samples flowing successively in each of the tubes 10, 12 and each separated from its neighbor by a wash liquid segment between a pair of gas segments. The sampler has twin sample probes side by side for concurrently aspirating fluids, the probes being coupled to the tube inlets 16 and 18, respectively. The samples, in which the probes are immersible, are supplied in discrete form from a series of sample cups supported from the sampler. By way of example, the samples are different samples of whole human blood treated with an appropriate anticoagulant, for the determination of the percentage volume of total cells in each sample, known as TCV.

Compressible pump tubes 20, 22 extend through the pump 14 and have inlet ends 24 and 26, respectively. The outlet ends of tubes 12 and 22 are coupled to tube 20 downstream of the pump 14, as shown. The inlet 24 is coupled in a nonillustrated manner to a source of diluent and the inlet 26 is exposed to ambient air. The diluent should be an isotonic solution and not cause a measurable electrolyte shift between the blood plasma and cells. For example, the diluent may be a 5% solution of Dextrose and water. The addition to the diluent of fixing agents, to prevent cell swelling, and inhibitors, to prevent active ion transport between the plasma and cells, are possible but have not been found necessary. The diluent stream in tube 20 is segmented by segments of air flowing from tube 22. The sample stream flowing in tube 20 is added to the air-segmented diluent stream and further segmented by the latter so that each sample contains air or gas segments. A mixing coil 28 is interposed in tube 20 to mix the sample and diluent therein. As shown in FIG. 1, flow-through electrode assemblies 30, 32 are interposed in tubes 10, 20, respectively, and the outlets of the tubes 10, 20 are directed to waste. For example, the pump tubes 10, 12, 20 and 22 provide flow rates of 0.166 ml/min., 0.226 ml/min., 0.482 ml/min., and 0.09 ml/min., respectively, by the action of the continuously operated pump 14.

Figure 2:
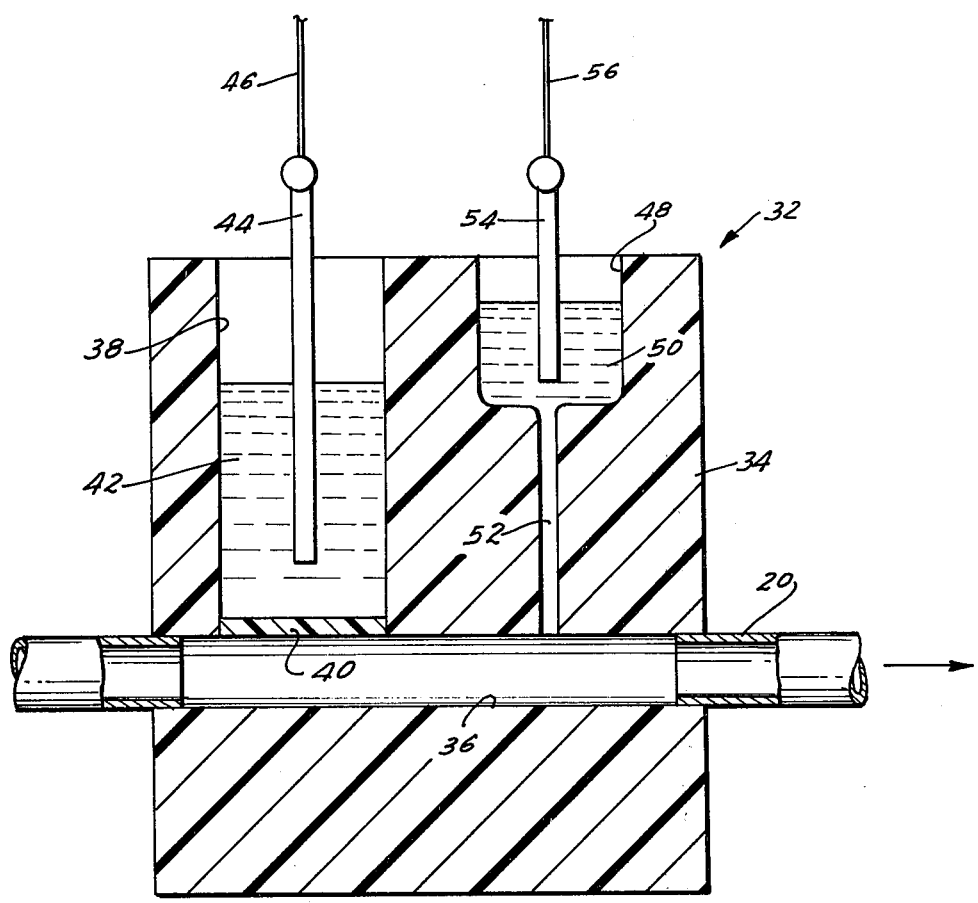
FIG. 2 is an enlarged median sectional view in side elevation illustrating somewhat diagrammatically one of the electrode assemblies of FIG. 1.

The electrode assembly 32, which is the twin of assembly 30, is best shown in FIG. 2 and comprises a nonconductive body 34 having a through passageway 36 interposed in tube 20. A vertical bore 38, extending downwardly to the passageway 36, has a membrane 40 of an ion-selective electrode fixed across the lower end of the bore 38 for contact at its lowest face by the aforementioned stream directed by the tube 20. For example, the membrane 40 may be selective to chloride ions which occur naturally in blood at significant levels, like sodium and potassium ions, and comprise a matrix of polyvinyl chloride impregnated with a tetraalkyl ammonium salt. A volume of an electrolyte filling solution 42 of potassium chloride for the internal reference electrode is in contact with the upper surface of the membrane 40 and is held captive in the bore 38. The ion-selective electrode or half cell is completed by an internal reference electrode 44 of silver-silver chloride wire which is shown extending into the solution 42 and having a terminal connected to a lead 46. The reference electrode portion of the assembly 32 comprises a cavity 48 in the body 34 filled with an electrolyte solution 50 of potassium chloride and having a leak junction with the passageway 36 provided by a passageway 52. An electrode 54 of silver-silver chloride extends into the solution 50 and has a terminal connected to a lead 56. The electrode assembly 30 has leads 58, 60 connected thereto which are the equivalents of the aforementioned leads 46 and 56, respectively.

The basis for measurement of TCV is a comparison of the sum of the total quantities of a particular ion present in a sample and a diluent with the measured quantity of that ion in a mixture of the sample and the diluent. The total quantity of an ion in a liquid medium is proportional to the ion concentration and to the volume of the medium. When the liquid medium contains particulate material, the total quantity of ion present is decreased by an amount proportional to the volume of the solid phase or particulate material. Comparison of the total ion quantity in a sample and a diluent before and after mixing allows the volume of the solid phase to be calculated. The ratio of the volume of the solid phase to the sample volume, expressed as a percentage, is the TCV.

According to the present invention, a known volume of sample (or a known sample flow rate in the case of a continuous-flow system), $V_1$, contains an unknown concentration of the particular ion $[X]_1$, which is to be measured and an unknown volume of particulate matter, $V_s$. In the case of blood samples, such particulate matter would include erythrocytes, leukocytes, platelets, etc. The total quantity of the ion in the sample is given by $(V_1 - V_s)[X]_1$. The sample is mixed with a known volume (or a known flow rate in a continuous-flow system) $V_2$ of a diluent containing a known concentration of the particular ion $[X]_2$; the the total quantity, therefore, of the particular ion in the diluent is $V_2[X]_2$. Thus, the total quantity of the particular ion in the diluted sample is the sum of the quantities in the sample and diluent, i.e., $(V_1 - V_s)[X]_1 + V_2[X]_2$. The concentration of the particular ion in the diluted sample has the measured value $[X]_3$, whereby the total quantity of the particular ion in the diluted sample is given by $(V_1 + V_2 - V_s)[X]_3$. Equating the sum of the quantities of the ion in the sample and the diluent with the total quantity of the ion in the mixture, i.e., $(V_1 - V_s)[X]_1 + V_2[X]_2 = (V_1 + V_2 - V_s)[X]_3$, allows the volume of particulate matter, $V_s$ to be calculated $$V_s = \frac{V_1[X]_1 + V_2[X]_2 - (V_1 + V_2)[X]_3}{[X]_1 - [X]_3} \quad (1)$$

The ratio of this particulate material volume to the sample volume gives the TCV:

$$\frac{TCV}{100} = \frac{V_1[X]_1 + V_2[X]_2 - (V_1 + V_2)[X]_3}{V_1[X]_1 - V_1[X]_3} \quad (2)$$

Equation two can be solved by the logic arrangement illustrated in FIG. 1. While the logic arrangement of FIG. 1 is illustrated as a digital system, it is obvious that the solution of the equation could be effected in analog fashion as well.

The signals generated by ion selective and reference electrode assemblies 30 and 32, representing the ion concentration in the sample and the sample-diluent mixture, respectively, are amplified and linearized by amplifiers 62 and 64, respectively. The amplifiers 62 and 64, preferably, have an anti-logarithmic characteristic, so as to compensate for nonlinearity in the response of the ion-selective electrodes. The amplified signals are applied to the input of conventional A/D converters 66 and 68, respectively. The coded output along lead 70, identified by $[X]_1$, indicates the total ion concentration measured in the blood sample; the coded output along lead 72, identified by $[X]_3$, indicates the total ion concentration measured in the mixture.

The signals $[X]_1$ and $[X]_3$ are acted upon and compared with known system constants so as to generate directly the total cell volume TCV. These constants are the respective volumes of the sample and diluent, $V_1$ and $V_2$, respectively, which are indicative of the respective flow rates in a continuous-flow system or the respective volumes in a discrete system, and the known concentration of the ion in the diluent $[X]_2$. For purposes of illustration, the constants $V_1$, $V_2$ and $[X]_2$ are introduced by means of thumbwheel switch arrangements 74, 76 and 78, respectively. In operation, the thumbwheel switch arrangements 74, 76 and 78 would be adjusted according to the particular ion to be measured, in this example chloride, by the electrode assemblies 30 and 32, and would be a part of the calibration sequence of the system.

Assuming that the sample and sample-diluent mixture are passing through the respective electrode assemblies 30 and 32, the outputs of A/D converters 66 and 68 would represent the quantities $[X]_1$ and $[X]_3$ corresponding to a particular sample, in binary numbers. The quantity $[X]_1$ is applied to a conventional multiplication circuit 80; the output of thumbwheel switch arrangement 74, i.e., $V_1$ is applied to the second input of the multiplication circuit 80. The product $V_1 [X]_1$ represents the apparent quantity of the ion present in the blood sample. Also, the output of thumbwheel switches 76 and 78 are applied to the inputs of a conventional multiplication circuit 82, to generate the product $V_2 [X]_2$, which represents the actual quantity of the ion in the diluent. The two steps described above provide information regarding the sample and diluent, prior to the mixing thereof.

Subsequent to the mixing of the sample and diluent, the output of A/D converter 68 represents the quantity $[X]_3$ and is applied to one input of the conventional multiplication circuit 84. The other input of multiplication circuit 84 is connected to the output of add circuit 86, whose inputs are connected to the respective outputs of the thumbwheel switches 74 and 76. Accordingly, the product $(V_1 + V_2) [X]_3$ is generated by multiplication circuit 84 and applied to one input of the conventional subtract circuit 88. The second input of subtract circuit 88 is connected to the output of add circuit 90, whose inputs are connected to the respective outputs of multiplication circuits 80 and 82. The output of the subtract circuit 88, therefore, represents the numerator of the equation, which is applied to the input of a conventional divide circuit 92.

To provide the denominator of the equation, subtract circuit 94 is provided, having inputs connected to the respective outputs of multiplication circuits 80 and 96. The inputs of multiplication circuit 96 are connected to the respective outputs of thumbwheel switch arrangement 74 and A/D converter 68, along lead 72. The output of multiplication circuit 96, when subtracted from the output of multiplication circuit 80, i.e., the quantity $V_1 [X]_1$, by subtract circuit 94 provides the denominator of the equation. The output of subtract circuit 94 is applied to the second input of divide circuit 92, whose output, when scaled by a factor of 100, is directly indicative of the TCV of the sample being measured. This quantity is applied to printer 98.

When the measured ion is not present at significant levels in the diluent, the thumbwheel switch 78 is set at zero; therefore, the equation solved by the apparatus of FIG. 1 becomes $[X]_2 = 0$ and $$\frac{TCV}{100} = \frac{V_1 [X]_1 - (V_1 + V_2) [X]_3}{V_1 [X]_1 - V_1 [X]_3} \qquad (3)$$

Further, when the measured ion is not naturally present at significant levels in the sample but is present at such levels as by spiking the diluent with a known concentration of that ion, switches 100 and 102 associated with leads 58 and 60, respectively, are closed to connect these leads to ground. Therefore, the equation solved the apparatus of FIG. 1 becomes $[X]_1 = 0$ and $$\frac{TCV}{100} = \frac{(V_1 + V_2) [X]_3 - V_2 [X]_2}{V_1 [X]_3} \qquad (4)$$

The difference between true hematocrit and TCV results from the presence of white cells, platelets etc. which for normal blood samples results in a difference less than the precision of measurement of either method. For example, TCV measurements based on chloride ion determination gave a standard deviation of 1.4% as compared to a manual packed cell volume method over the hemotocrit range 14 to 71%.

While the invention has been described with reference to TCV of whole blood, it is to be understood that TCV equals the percentage volume of total particulate or solid phases in other liquid media, and may be employed, for example, in the determination, in a batch process, of the total solids in a soup expressed as a percentage volume of the total sample volume.

While several forms of the invention have been described, it will be apparent especially to those versed in the art, that the invention may take other forms and is susceptible to various changes in details without departing from the principles of the invention.

What is claimed is:

1. A method for determining the percentage total volume of particulates in a liquid sample, comprising the steps of: introducing a predetermined volume of a diluent having a known concentration of a particular ion into a predetermined volume of said sample having a known concentration of said particular ion, and determining the total liquid volume of said sample including measuring the concentration of said particular ion in the diluted sample.

2. A method as defined in claim 1 wherein: the concentration of said particular ion in said sample is insignificant.

3. A method as defined in claim 1, wherein: the concentration of said ion in said diluent is insignificant.

4. A method as defined in claim 1, wherein: the concentration of said particular ion in said sample is significant, and including the further step of measuring the concentration of said particular ion in said predetermined volume of said sample to render said concentration known.

5. A method as defined in claim 1, further including the steps of passing predetermined volumes of successive liquid samples along a conduit, said samples having known concentrations of said particular ion, introducing a predetermined volume of said diluent into each successive sample volume so as to be mixed therewith, and measuring the concentration of said particular ion in said diluted samples, in turn.

6. A method as defined in claim 1, further including the steps of passing predetermined volumes of successive liquid samples along a first conduit, said samples having unknown concentrations of said particular ion, passing successive mixtures comprising predetermined volumes of said sample and diluent along a second conduit, measuring the concentration of said particular ion in said successive samples and in said successive mixtures, and deriving the percentage total volume of particulates in said successive samples from said measurements.

7. A method for determining the percentage total volume of particulates in whole blood samples containing an anticoagulant and a known concentration of a particular ion, comprising the steps of: passing predetermined volumes of said samples along a first conduit, introducing a known volume of a diluent isotonic to blood into said conduit to be mixed with each of said samples, said diluent having a known concentration of said particular ion, and determining the total liquid volume of said sample including measuring the concentration of said ion in each sample-diluent mixture.

8. A method as defined in claim 7, wherein: the concentration of said ion in said sample is insignificant.

9. A method as defined in claim 7, wherein: the concentration of said ion in said diluent is insignificant.

10. A method as defined in claim 7, further including passing additional predetermined volumes of said samples along a second conduit, measuring the concentration of said particular ion in each of said samples in said second conduit, and deriving the percentage total volume of particulates in each sample from these measurements.

11. Apparatus for determining the percentage total volume of particulates in a liquid sample, comprising: means for mixing in sample-support means a predetermined volume of diluent having a known concentration of a particular ion and a predetermined volume of said sample having a known concentration of said particular ion, and means determining the total liquid volume of said sample including means measuring the concentration of said particular ion in said diluted sample.

12. Apparatus as defined in claim 11, wherein: said sample has a concentration of said particular ion which is significant, and further including support means for a predetermined volume of said sample, means measuring the concentration of said particular ion in said sample to render said concentration known, and means deriving the percentage total volume of particulates in each of said samples from said measurements.

13. Apparatus as defined in claim 11, wherein: said mixing means includes means for flowing predetermined volumes of successive samples along a first conduit, and means for introducing a predetermined volume of said diluent into each of said samples in said first conduit.

14. Apparatus as defined in claim 11, wherein: said measuring means comprises an ion-selective and a reference electrode.

15. Apparatus as defined in claim 12, wherein: each of said measuring means comprises an ion-selective and a reference electrode.

16. Apparatus as defined in claim 13, further including means flowing a second predetermined volume of successive samples along a second conduit, means measuring the concentration of said particular ion in said samples in said second conduit to render said concentration known, and means deriving the percentage total volume of particulates in said samples from said measurements.

17. Apparatus as defined in claim 13, further including means for recording the percentage total volume of particulates in each of said samples.

18. Apparatus as defined in claim 16, wherein: said means measuring said concentration of said particular ion in said samples and in said sample-diluent mixtures are operative in parallel.

19. Apparatus as defined in claim 16, wherein: each of said measuring means comprises an ion-selective and a reference electrode.

* * * * *